(12) United States Patent
Schneider et al.

(10) Patent No.: US 9,517,573 B2
(45) Date of Patent: Dec. 13, 2016

(54) METHOD AND APPARATUS FOR CUTTING A SUBSTRATE

(71) Applicant: The Procter & Gamble Company, Cincinnati, OH (US)

(72) Inventors: Uwe Schneider, Cincinnati, OH (US); Daniel Patrick Findley, Finneytown, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 253 days.

(21) Appl. No.: 14/038,848

(22) Filed: Sep. 27, 2013

(65) Prior Publication Data

US 2014/0109736 A1  Apr. 24, 2014

Related U.S. Application Data

(60) Provisional application No. 61/717,290, filed on Oct. 23, 2012.

(51) Int. Cl.
 *B26D 1/40* (2006.01)
 *B26D 5/02* (2006.01)
 (Continued)

(52) U.S. Cl.
 CPC .......... *B26D 1/405* (2013.01); *A61F 13/15723* (2013.01); *B26D 1/40* (2013.01);
 (Continued)

(58) Field of Classification Search
 CPC ........... B26D 1/405; B26D 7/265; B26D 1/40; B26D 5/02; B26D 7/2628; B26D 2007/2664; Y10T 83/4708; Y10T 83/4711; Y10T 83/4838; Y10T 83/04; B26F 1/20; B26F 1/384; A61F 13/15723
 (Continued)

(56) References Cited

U.S. PATENT DOCUMENTS 5,207,138 A    5/1993  Sato et al.
5,918,518 A *  7/1999  Kobayashi ............ B26D 1/405
                                                    83/100
(Continued)

FOREIGN PATENT DOCUMENTS

EP    0 534 177 A1    3/1993
EP    1 798 011 A1    6/2007
(Continued)

OTHER PUBLICATIONS

PCT International Search Report PCT/US2003/065871, dated Feb. 12, 2014, 10 pages.
(Continued)

*Primary Examiner* — Ghassem Alie
*Assistant Examiner* — Nhat Chieu Do
(74) *Attorney, Agent, or Firm* — Sarah M. DeCristofaro; Abbey A. Lopez

(57) ABSTRACT

A rotary cutting apparatus is configured to rotate about a first longitudinal axis. The cutting roll includes a cutting member. The apparatus includes an anvil roll that is configured to rotate about a second longitudinal axis. The anvil roll is positioned relative to the cutting roll such that the first longitudinal axis is substantially parallel with the second longitudinal axis. The anvil roll includes an outer circumferential surface. The second longitudinal axis is selectively movable between a first position and a second position relative to the first longitudinal axis. In the first position, a first minimum distance is defined between the first longitudinal axis and the second longitudinal axis. In the second position, a second minimum distance is defined between the first longitudinal axis and the second longitudinal axis, and wherein the second minimum distance is greater than the first minimum distance.

8 Claims, 14 Drawing Sheets

(51) Int. Cl.
*B26D 7/26* (2006.01)
*A61F 13/15* (2006.01)
*B26F 1/38* (2006.01)

(52) U.S. Cl.
CPC ............ *B26D 5/02* (2013.01); *B26D 7/2628* (2013.01); *B26D 7/265* (2013.01); *B26D 2007/2664* (2013.01); *B26F 1/384* (2013.01); *Y10T 83/04* (2015.04); *Y10T 83/4838* (2015.04)

(58) Field of Classification Search
USPC .................................................. 83/304–305
See application file for complete search history.

(56) References Cited

U.S. PATENT DOCUMENTS

| | | | | |
|---|---|---|---|---|
| 6,418,827 | B1 * | 7/2002 | Bussey, III et al. | ..... B26D 5/02 83/304 |
| 7,569,039 | B2 | 8/2009 | Matsuda et al. | |
| 2003/0035143 | A1 | 2/2003 | Glemser et al. | |
| 2003/0159558 | A1 * | 8/2003 | Takayama | ............ B26D 7/1854 83/100 |
| 2005/0103173 | A1 | 5/2005 | Elkis et al. | |
| 2005/0107764 | A1 | 5/2005 | Matsuda et al. | |
| 2007/0219521 | A1 | 9/2007 | Hird et al. | |
| 2011/0139657 | A1 | 6/2011 | Hird et al. | |
| 2011/0139658 | A1 | 6/2011 | Hird et al. | |
| 2011/0139659 | A1 | 6/2011 | Hird et al. | |
| 2011/0139662 | A1 | 6/2011 | Hird et al. | |
| 2011/0152812 | A1 | 6/2011 | Hird et al. | |
| 2011/0277606 | A1 * | 11/2011 | Park | ..................... B26D 7/2614 83/100 |
| 2012/0061015 | A1 | 3/2012 | LaVon et al. | |
| 2012/0061016 | A1 | 3/2012 | LaVon et al. | |

FOREIGN PATENT DOCUMENTS

| | | |
|---|---|---|
| GB | 2 458 686 A1 | 9/2009 |
| JP | 62-188697 | 8/1987 |
| JP | 2003-20635 U | 1/2003 |
| JP | 2005-340773 A | 12/2005 |

OTHER PUBLICATIONS

PCT International Search Report PCT/US2003/066000, dated Feb. 12, 2014, 9 pages.
U.S. Appl. No. 14/038,843, filed Sep. 27, 2013, Uwe Schneider.

* cited by examiner

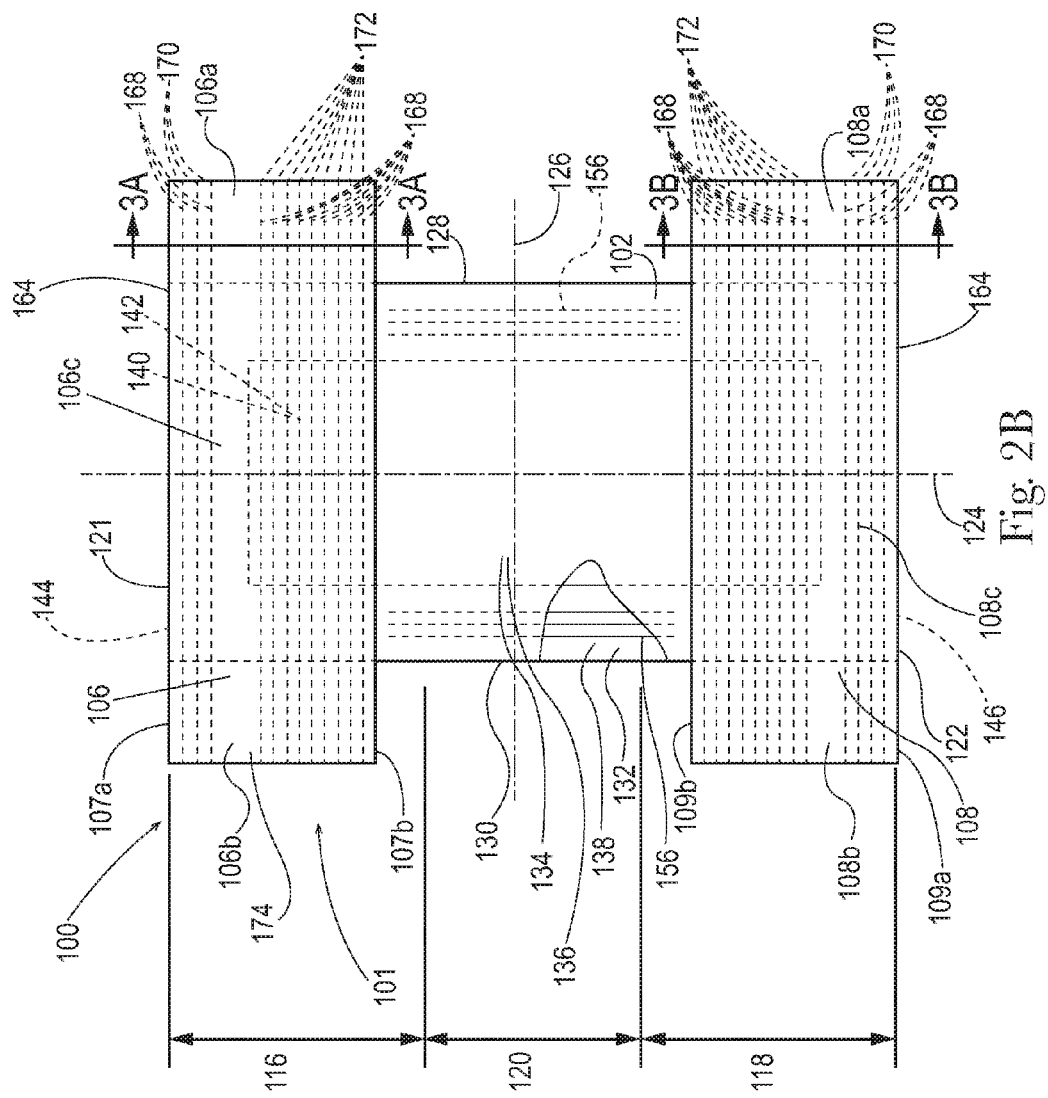

METHOD AND APPARATUS FOR CUTTING A SUBSTRATE

FIELD OF THE INVENTION

The present disclosure relates to methods and apparatuses for manufacturing absorbent articles, and more particularly, to methods and apparatuses for cutting a substrate.

BACKGROUND OF THE INVENTION

Along an assembly line, various types of articles, such as diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some processes, a continuous length of diaper assemblies advancing in a machine direction is cut into discrete assemblies and combined with continuous lengths of elastically extendable front and back waistband webs advancing in a machine direction. In some processes, the continuous length of diaper assemblies may advance to a rotary cutting apparatus. Sometimes, the continuous length of diaper assemblies may undesirably break as the diaper assemblies advance in the machine direction toward the rotary cutting apparatus. As a result, the continuous length of diaper assemblies may jam and/or wrap around equipment. The converting line may need to be shut down in order to remove jams and/or wraps of diaper assemblies and to rethread the continuous diaper assemblies, while bypassing the rotary cutting apparatus. In some processes, when the converting line is turned back on, the continuous length of diaper assemblies is hand-pulled from the converting line until the continuous length of diaper assemblies reach a desired quality. Once the continuous length of diaper assemblies reaches a desired quality, the line may be shut down again in order to rethread the continuous length of diaper assemblies through the rotary cutting apparatus. The converting line may then be restarted. Once the converting line is restarted, it may take several minutes for the continuous length of diaper assemblies to reach a desired quality. The process of shutting down a converting apparatus, rethreading the continuous length of diaper assemblies, and restarting the converting apparatus can take away from production time.

Therefore, it would be beneficial to provide a process and apparatus for reduces the number of shut downs required to restart a converting apparatus.

SUMMARY OF THE INVENTION

The present disclosure includes a rotary cutting apparatus that is selectively configurable to operate in a substrate cutting configuration and a substrate bypass configuration. The rotary cutting apparatus comprises a cutting roll defining a first longitudinal axis, wherein the cutting roll is configured to rotate about the first longitudinal axis, the cutting roll comprising a cutting member. The rotary cutting apparatus further comprises an anvil roll defining a second longitudinal axis, wherein the anvil roll is configured to rotate about the second longitudinal axis. The anvil roll is positioned relative to the cutting roll such that the first longitudinal axis is substantially parallel with the second longitudinal axis. The anvil roll comprises an outer circumferential surface. The second longitudinal axis is selectively movable between a first position and a second position relative to the first longitudinal axis. When the second longitudinal axis is moved to the first position, a first minimum distance is defined between the first longitudinal axis and the second longitudinal axis. When the second longitudinal axis is moved to the second position, a second minimum distance is defined between the first longitudinal axis and the second longitudinal axis. The second minimum distance is greater than the first minimum distance.

Aspects of the present disclosure include a method comprising the steps of: advancing a substrate in a machine direction to a rotary cutting apparatus, the rotary cutting apparatus comprising a cutting roll and an anvil roll; rotating the cutting roll about a first longitudinal axis; rotating the anvil roll about a second longitudinal axis adjacent to the cutting roll, wherein the anvil roll is positioned relative to the cutting roll such that the first longitudinal axis is substantially parallel with the second longitudinal axis; placing the rotary cutting apparatus in a first configuration by moving the second longitudinal axis to a first position; cutting the substrate with the rotary cutting apparatus in the first configuration; placing the rotary cutting apparatus in a second configuration by moving the second longitudinal axis to a second position; and advancing the continuous substrate through the rotary cutting apparatus in the second configuration without cutting the continuous substrate.

Aspects of the present disclosure include a method comprising the steps of: rotating a cutting roll about a first longitudinal axis; rotating an anvil roll about a second longitudinal axis, wherein the anvil roll is positioned relative to the cutting roll such that the first longitudinal axis is substantially parallel with the second longitudinal axis, wherein the first longitudinal axis is located a first minimum distance from the second longitudinal axis; advancing a continuous substrate in a machine direction between the anvil roll and the cutting roll with the first longitudinal axis located at the first minimum distance from the second longitudinal axis; cutting the continuous substrate into discrete components; positioning the anvil roll such that the first longitudinal axis is located a second minimum distance from the second longitudinal axis, wherein the second minimum distance is greater than the first minimum distance; and advancing the continuous substrate in the machine direction between the cutting roll and the anvil roll with the first longitudinal axis located at the second minimum distance from the second longitudinal axis, wherein the continuous substrate is not cut by the cutting roll.

BRIEF DESCRIPTION OF THE DRAWINGS

FIG. 2B is a partially cut-away, plan view of a diaper pant.

DETAILED DESCRIPTION OF THE INVENTION

Figure 1:
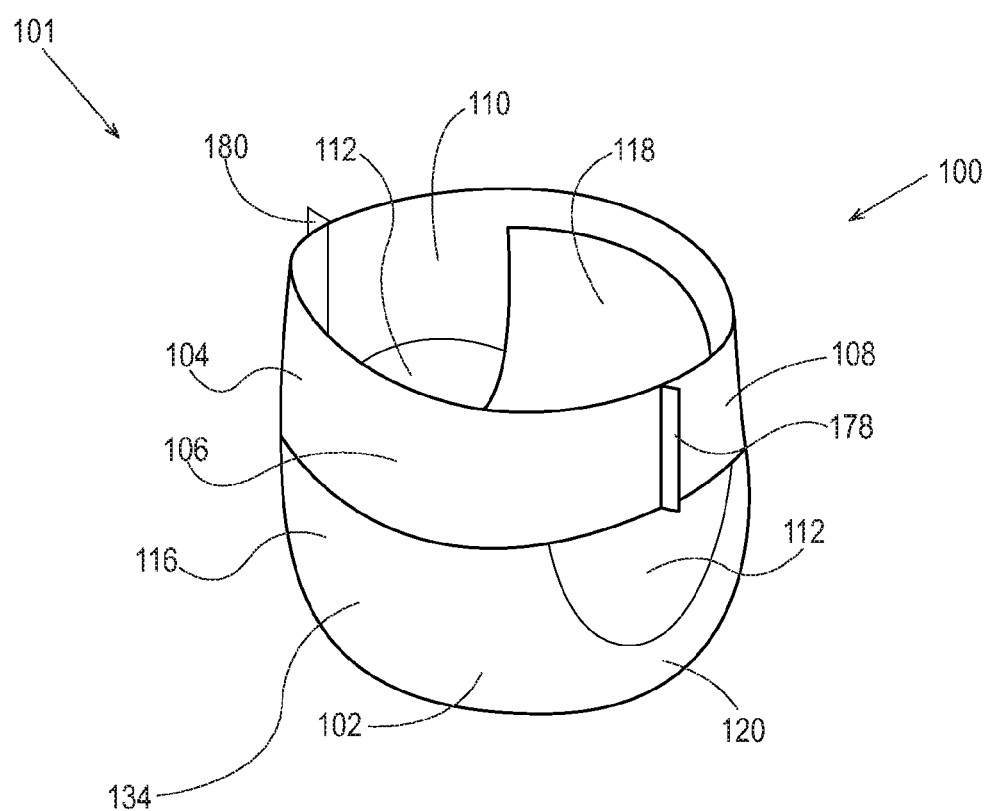
FIG. 1 is a schematic, perspective view of a diaper pant.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" refers herein to a material that is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Machine direction" (MD) refers herein to the direction of material flow through a process. In addition, relative placement and movement of material can be described as flowing in the machine direction through a process from upstream in the process to downstream in the process.

"Cross direction" (CD) refers herein to a direction that is not parallel with, and usually perpendicular to, the machine direction.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. Pant diapers can be preformed anywhere along the circumference of the waist region (e.g., side fastened or connected, front waist fastened or connected, rear waist fastened or connected).

Aspects of the present disclosure involve methods and apparatuses for manufacturing absorbent articles, and more particularly, methods and apparatuses for restarting a converting line during the manufacturing absorbent articles. The methods and apparatuses disclosed herein operate to advance a continuous length of diaper assemblies through a rotary cutting apparatus. The rotary cutting apparatus may be selectively configurable to operate in a first configuration, referred to herein as a substrate cutting configuration, and a second configuration, referred to herein as a substrate bypass configuration. The rotary cutting apparatus includes a cutting roll defining a first longitudinal axis, wherein the cutting roll includes a cutting member and is configured to rotate about the first longitudinal axis. The rotary cutting apparatus also includes an anvil roll defining a second longitudinal axis, wherein the anvil roll includes an outer circumferential surface and is configured to rotate about the second longitudinal axis. The anvil roll is positioned relative to the cutting roll such that the first longitudinal axis is substantially parallel with the second longitudinal axis.

The second longitudinal axis is selectively movable between a first position and a second position relative to the first longitudinal axis. When the second longitudinal axis is moved to the first position, a first minimum distance is defined between the first longitudinal axis and the second longitudinal axis. When the second longitudinal axis is moved to the second position, a second minimum distance is defined between the first longitudinal axis and the second longitudinal axis. The second minimum distance is greater than the first minimum distance. With the rotary cutting apparatus in the substrate cutting configuration, the second longitudinal axis is located in the first position. With the rotary cutting apparatus in the substrate bypass configuration, the second longitudinal axis is located in the second position.

In operation, a continuous length of chassis assemblies is advanced in a machine direction to a rotary cutting apparatus. The cutting roll is rotated about the first longitudinal axis. The anvil roll is rotated about the second longitudinal axis adjacent to the cutting roll. When the rotary cutting apparatus is configured in the substrate cutting configuration, the rotary cutting apparatus cuts the continuous length of chassis assemblies into discrete chassis. When the rotary cutting apparatus is configured in the substrate bypass configuration, the continuous length of chassis assemblies advances through the rotary cutting apparatus without cutting the continuous length of chassis assemblies.

As previously mentioned, the methods and apparatuses discussed herein may be used to manufacture absorbent articles. To help provide additional context to the subsequent discussion of the process embodiments, the following provides a general description of absorbent articles in the form of diaper pants that may be manufactured in accordance with the methods and apparatuses disclosed herein. While the present disclosure relates to cutting continuous lengths of chassis assemblies for diaper pants, it is to be appreciated that the methods and apparatuses disclosed herein may be used with various types of absorbent articles in folded or unfolded configurations.

Figure 2A:
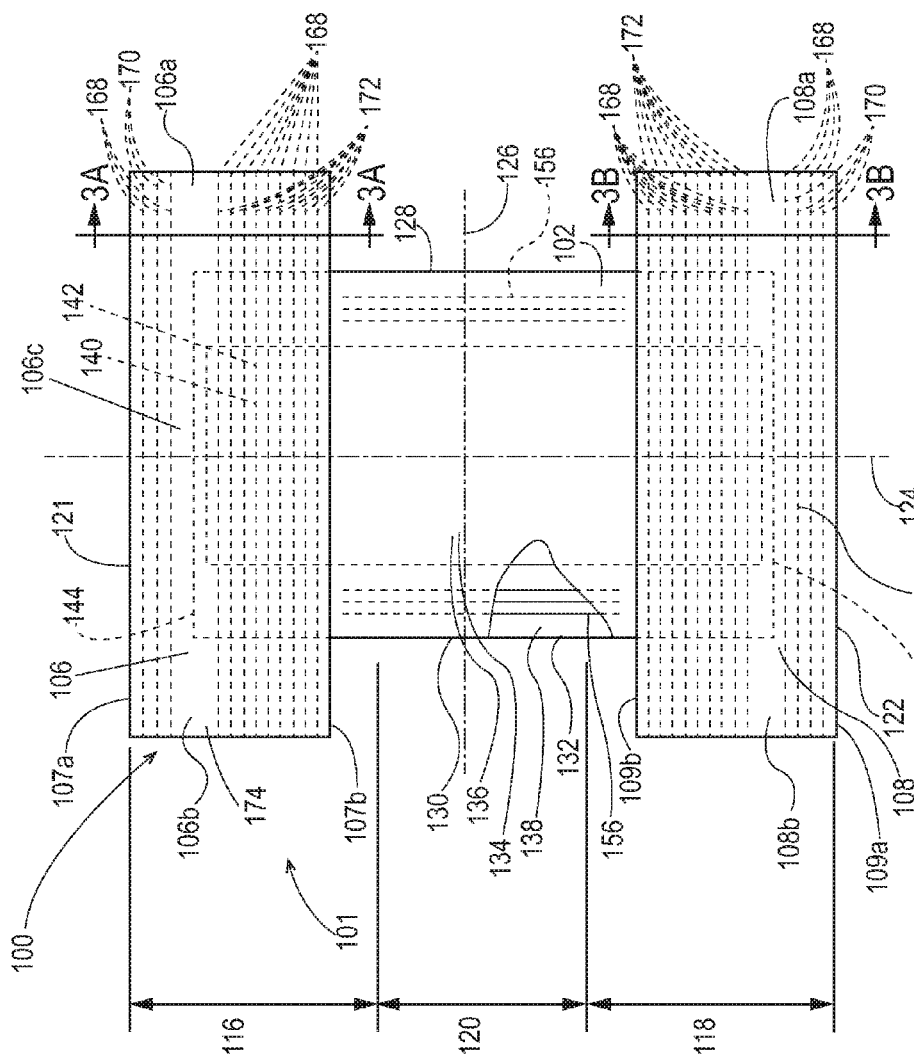
FIG. 2A is a partially cut-away, plan view of a diaper pant.

FIGS. 1 and 2A show an example of an absorbent article 100 shown in the form of a diaper pant 101 that may be formed in accordance with the apparatuses and methods disclosed herein. In particular, FIG. 1 shows a perspective view of a diaper pant 101 in a pre-fastened configuration and FIG. 2A shows a plan view of the diaper pant 101 with the portion of the diaper pant 101 that faces away from a wearer oriented toward the viewer. The diaper pant 101 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 120 disposed intermediate the first and second waist regions 116 and 118. The first waist region 116 may be configured as a front waist region, and the second waist region 118 may be configured as back waist region. In some embodiments, the length of each of the front waist region 116, back waist region 118, and crotch region 120 may be one-third of the length of the absorbent article 100. The diaper pant 101 may also include a laterally extending front waist edge 121 in the front waist region 116 and a longitudinally opposing and laterally extending back waist edge 122 in the back waist region 118. To provide a frame of reference for the present discussion, the diaper 101 and chassis 102 of FIG. 2A are shown with a longitudinal axis 124 and a lateral axis 126. In some embodiments, the longitudinal axis 124 may extend through the front waist edge 121 and through the back waist edge 122. The lateral axis 126 may extend through a first longitudinal or right side edge 128 and through a midpoint of a second longitudinal or left side edge 130 of the chassis 102.

As shown in FIGS. 1 and 2A, the diaper pant 101 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper pant 101 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 101 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

Referring to FIG. 2A, the diaper pant 101 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions.

Diaper pants may be manufactured with a ring-like elastic belt 104 and provided to consumers in a configuration wherein the front waist region 116 and the back waist region 118 are connected to each other as packaged, prior to being applied to the wearer. As such, diaper pants 101 may have a continuous perimeter waist opening 110 and continuous perimeter leg openings 112 such as shown in FIG. 1. The ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c. The central region 106c of the first elastic belt 106 is connected with the first waist region 116 of the chassis 102, and the central region 108c of the second elastic belt 108 is connected with the second waist region 118 of the chassis 102. FIGS. 1 and 2A, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

Figure 3A:
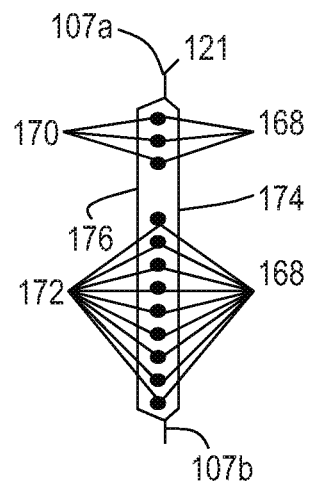
FIG. 3A is a cross-sectional view of the diaper pant of FIGS. 2A and 2B taken along line 3A-3A.
Figure 3B:
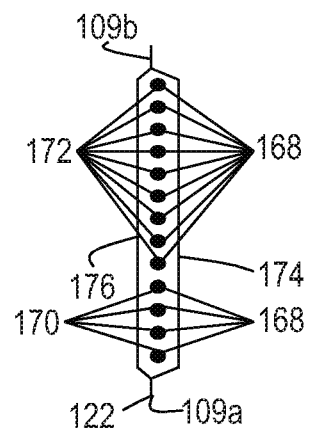
FIG. 3B is a cross-sectional view of the diaper pant of FIGS. 2A and 2B taken along line 3B-3B.

Referring to FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt 106 and the second elastic belt 108 may also each include an outer, garment facing layer 174 and an inner, wearer facing layer 176. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 174 and the inner layer 176. The belt elastic material may include one or more elastic elements such as strands, ribbons, or panels extending along the lengths of the elastic belts. As shown in FIGS. 2A, 3A, and 3B, the belt elastic material may include a plurality of elastic strands 168, which may be referred to herein as outer, waist elastics 170 and inner, waist elastics 172. As shown in FIG. 2A, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer 174 and the uncontracted inner layer 176. When the belt elastic material is relaxed, the belt elastic material returns to an unstretched condition and contracts the outer layer 174 and the inner layer 176. The belt elastic material may provide a desired variation of contraction force in the area of the ring-like elastic belt.

It is to be appreciated that the chassis 102 and elastic belts 106, 108 may be configured in different ways other than as depicted in FIG. 2A. For example, FIG. 2B shows a plan view of a diaper pant 101 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

Figure 4A:
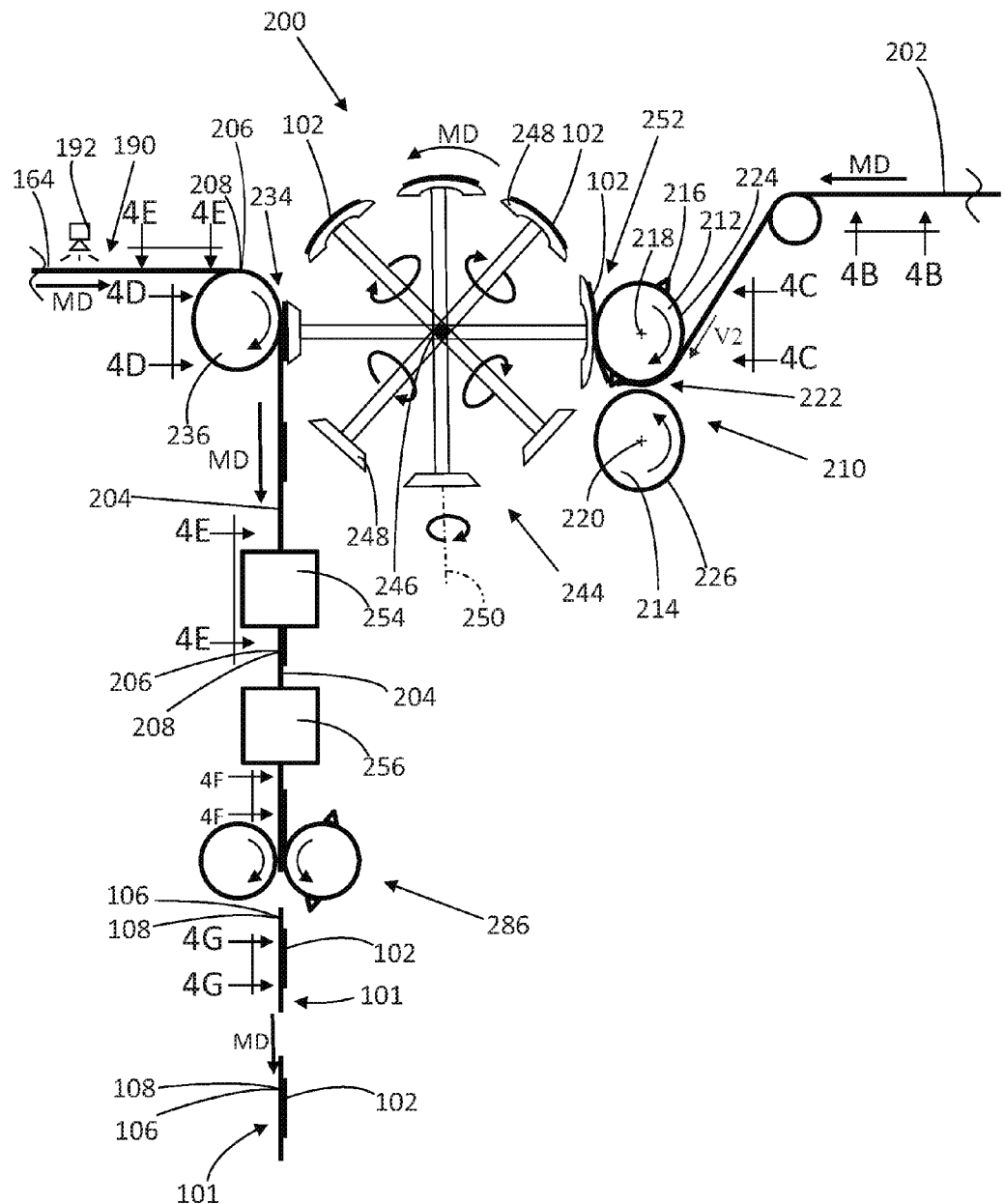
FIG. 4A is a schematic, side elevation view of a converting apparatus.

The apparatuses and methods of the present disclosure may be utilized to assemble various components of pre-fastened diaper pants 101. For example, FIG. 4A shows a schematic view of a converting apparatus 200 adapted to manufacture diaper pants 101. The method of operation of the converting apparatus 200 may be described with reference to the various components of diaper pant 101 described above and shown in FIGS. 1 and 2A. Although the following methods are provided in the context of the diaper pants 101 shown in FIGS. 1 and 2A, it is to be appreciated that various embodiments of diaper pants can be manufactured according the methods disclosed herein, such as for example, the absorbent articles disclosed in U.S. Pat. No. 7,569,039, filed on Nov. 10, 2004; U.S. Patent Publication No. 2005/0107764, published May 19, 2005; U.S. Patent Application No. 2012/0061016, published Mar. 15, 2012; and U.S. Patent Publication No. 2012/0061015, published Mar. 15, 2012.

With reference to FIG. 4A, and as described in more detail below, a converting apparatus 200 operates to advance continuous lengths of chassis assemblies 202 along a machine direction MD such that the longitudinal axis 124 is parallel with the machine direction MD. The continuous length of chassis assemblies 202 are cut into discrete chassis 102. The discrete chassis 102 are then rotated and advanced in the machine direction MD such that the lateral axis 126 is parallel with the machine direction MD. The discrete chassis 102 are combined with continuous lengths of advancing first and second elastic belt substrates 206, 208. The discrete chassis 102 are then folded along the lateral axis 126 to bring the first and second elastic belt substrates 206, 208 into a facing relationship. The first and second elastic belt substrates 206, 208 are then bonded together to form bonded regions 160. The first and second elastic belt substrates 206, 208 are then cut along the bonded regions 160 to create discrete diaper pants 101.

Figure 4B:
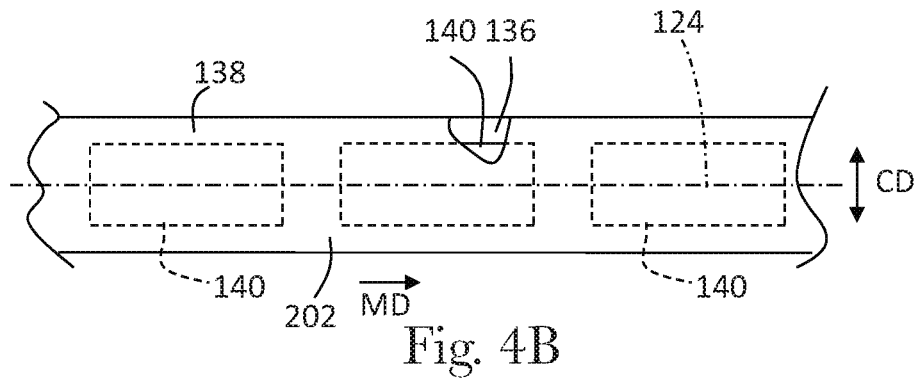
FIG. 4B is a schematic, plan view of a continuous length of chassis assemblies taken along line 4B-4B in FIG. 4A.

As shown in FIGS. 4A and 4B, a continuous length of chassis assemblies 202 is advanced in a machine direction MD to a rotary cutting apparatus 210. The rotary cutting apparatus 210 includes a cutting roll 212 and an anvil roll 214 that are rotatably. The cutting roll 212 defines a first longitudinal axis 218 and the anvil roll 214 defines a second longitudinal axis 220. The anvil roll 214 is positioned relative to the cutting roll 212 such that the first longitudinal axis 218 is substantially parallel with the second longitudinal axis 220. The cutting roll 212 and the anvil roll 214 are defined by outer circumferential surfaces 224 and 226, respectively. A cutting member 216 may extend radially outward from the outer circumferential surface 224 of the cutting roll 212. The cutting roll 212 may be configured to apply negative, vacuum pressure and/or positive, blow-off pressure through the outer circumferential surface 224 of the cutting roll 212.

Figure 4C:
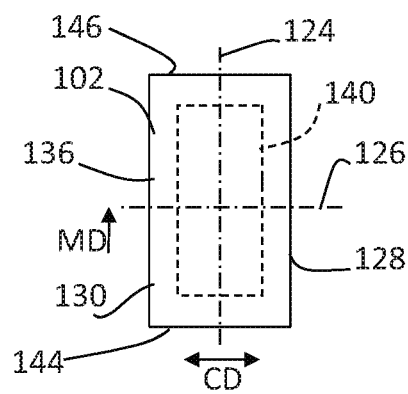
FIG. 4C is a schematic, plan view of a discrete chassis taken along line 4C-4C in FIG. 4A.

The continuous length of chassis assemblies 202 advances onto the outer circumferential surface 224 of the cutting roll 212. The continuous length of chassis assemblies 202 then advances through a nip 222 formed between the cutting roll 212 and the anvil roll 214. The cutting member 216 compresses the continuous length of chassis assemblies 202 against the outer circumferential surface 226 of the anvil roll 214 to separate the continuous length of chassis assemblies 202 into discrete chassis 102, such as shown in FIG. 4C. The continuous length of chassis assemblies 202 may include absorbent assemblies sandwiched between topsheet material and backsheet material, leg elastics, barrier leg cuffs and the like.

Figure 7:
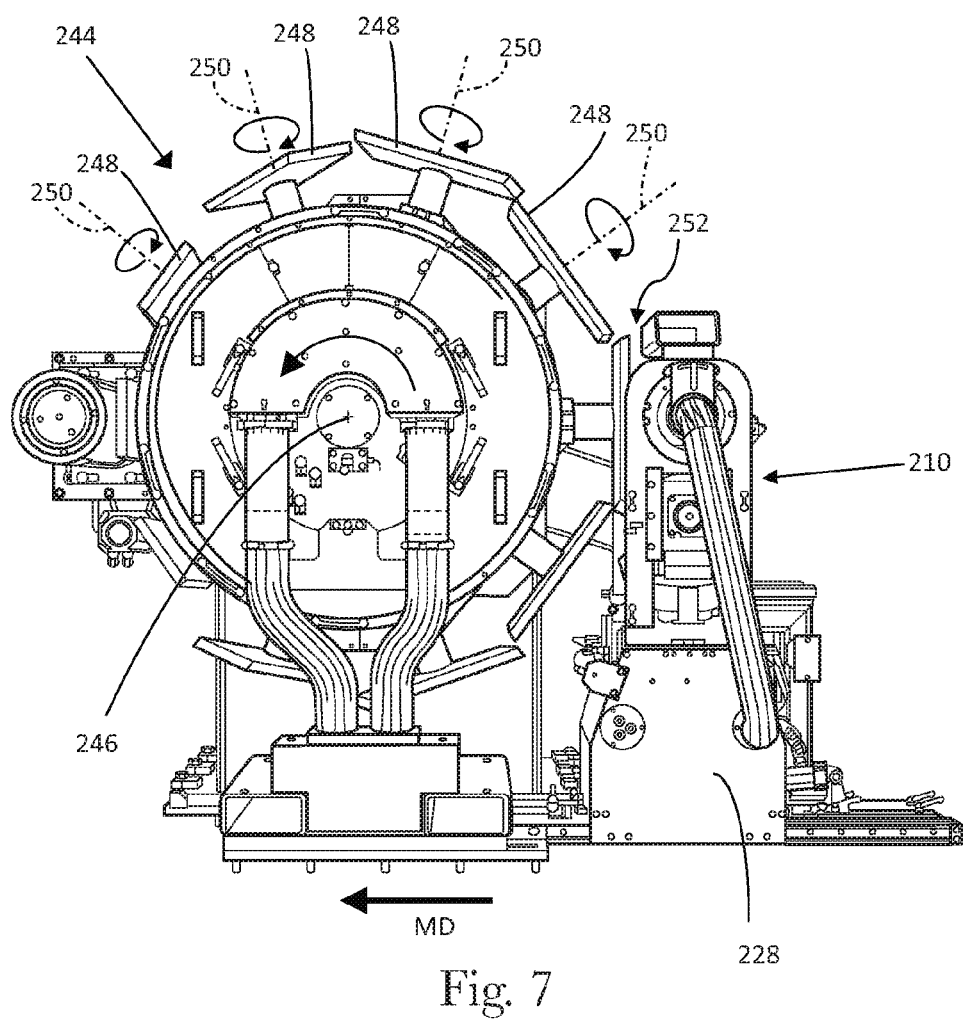
FIG. 7 is a side, elevation view of a rotary cutting apparatus and a transfer apparatus.

With continued reference to FIG. 4A, the discrete chassis 102 is transferred from the rotary cutting apparatus 210 to the transfer apparatus 244. With reference to FIGS. 4A and 7, the transfer apparatus 244 may rotate about a longitudinal axis 246 and may include a plurality of transfer members 248. The transfer members 248 may rotate about an axis of rotation 250 that is orthogonal to the longitudinal axis 246. As the discrete chassis 102 approaches the transfer apparatus 244, vacuum may be intermittently interrupted from the cutting roll 212, while at the same time positive blow-off pressure may be applied to the discrete chassis 102 from the outer circumferential surface 224 of the cutting roll 212 to assist the discrete chassis 102 in transferring from the cutting roll 212. The transfer members 248 may be configured with vacuum to hold the discrete chassis 102. Once the discrete chassis 102 is removed from the cutting roll 212, the cutting roll 212 continues to rotate in order to advance and cut a subsequent discrete chassis.

Figure 4D:
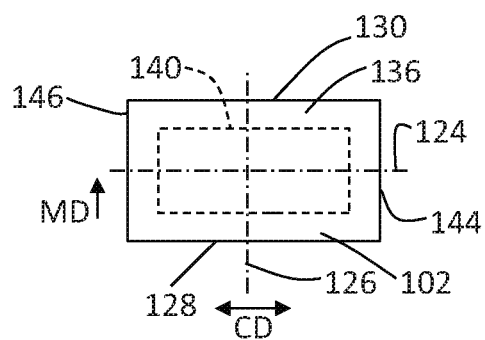
FIG. 4D is a schematic, plan view of a discrete chassis taken along line 4D-4D in FIG. 4A.

The discrete chassis 102 advances onto the transfer members 248 in the orientation shown in FIG. 4C where the longitudinal axis 124 is parallel with the machine direction MD. The transfer apparatus 244 shown in FIGS. 4A and 7 operates to advance the discrete chassis 102 in the machine direction MD while concurrently rotating the discrete chassis 102. The transfer apparatus 244 may rotate the discrete chassis 102 to the orientation shown in FIG. 4D where the lateral axis 126 is parallel with the machine direction MD. It is to be appreciated that various forms of transfer apparatuses may be used with the methods and apparatuses disclosed herein, such as methods and apparatuses for transferring discrete articles disclosed in U.S. patent application Ser. No. 13/447,531, filed on Apr. 16, 2012; U.S. patent application Ser. No. 13/447,544, filed on Apr. 16, 2012; U.S. patent application Ser. No. 13/447,568, filed on Apr. 16, 2012; and U.S. patent application Ser. No. 13/447,585, filed on Apr. 16, 2012.

Figure 4E:
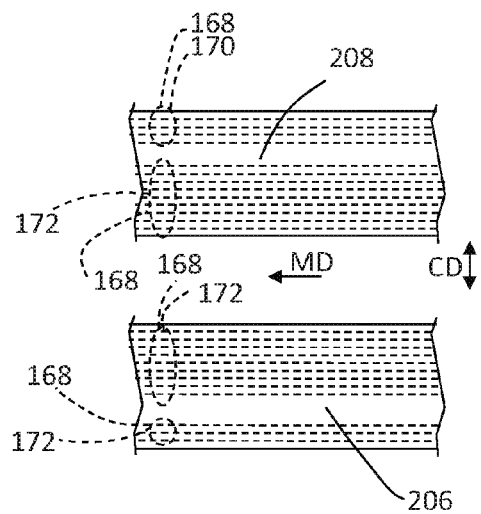
FIG. 4E is a schematic, plan view of a continuous length of first and second elastic belt substrates taken along line 4E-4E in FIG. 4A.
Figure 4F:
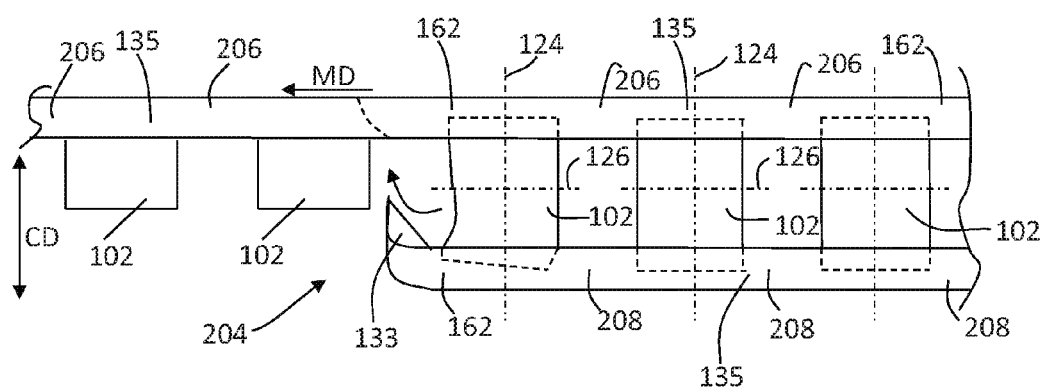
FIG. 4F is a schematic, plan view of a continuous length of absorbent articles taken along line 4F-4F in FIG. 4A.

As shown in FIG. 4A, the discrete chassis 102 is transferred from the transfer apparatus 244 and combined with advancing, continuous lengths of first and second belt substrates 206, 208, such as shown in FIG. 4E. The continuous lengths of first and second belt substrates 206, 208 are subsequently cut to form first and second elastic belts 106, 108 on diaper pants 101. The discrete chassis 102 are transferred from the transfer apparatus 244 to a nip 234 formed between the transfer apparatus 244 and a carrier apparatus 236. At the nip 234, the discrete chassis 102 is combined with the continuous lengths of advancing first and second belt substrates 206, 208 to form a continuous length of absorbent articles 204. As shown in FIGS. 2A, 2B, 3A, and 3B, a wearer facing surface 133 of the first belt substrate 206 may be combined with the garment facing surface 134 of the chassis 102 along the first waist region 116, and a wearer facing surface 133 of the second belt substrate 208 may be combined with the garment facing surface 134 of the chassis 102 along the second waist region 118. As shown in FIG. 4A, adhesive 190 may be applied to the wearer facing surface 133 of the first and second belt substrates 206, 208 using an adhesive applicator 192 before combining with the discrete chassis 102 at the nip 234. With reference to FIG. 4F, a continuous length of absorbent articles 204 is defined by multiple discrete chassis 102 spaced apart from each other along the machine direction MD and connected with each other by the first and second belt substrates 206, 208.

As shown in FIG. 4A, the continuous length of absorbent articles 204 advances from the nip 234 to a folding apparatus 254. With reference to FIG. 4F, at the folding apparatus 254, each chassis 102 is folded in the cross direction CD along a lateral axis 126 to place the first waist region 116, and specifically, the inner, wearer facing surface 132 into a facing, surface to surface arrangement with the inner, wear facing surface 132 of the second waist region 118. The folding of the chassis 102 also positions the wearer facing surface 133 of first belt substrate 206 in a facing relationship with the wearer facing surface 133 of the second belt substrate 208.

Figure 4G:
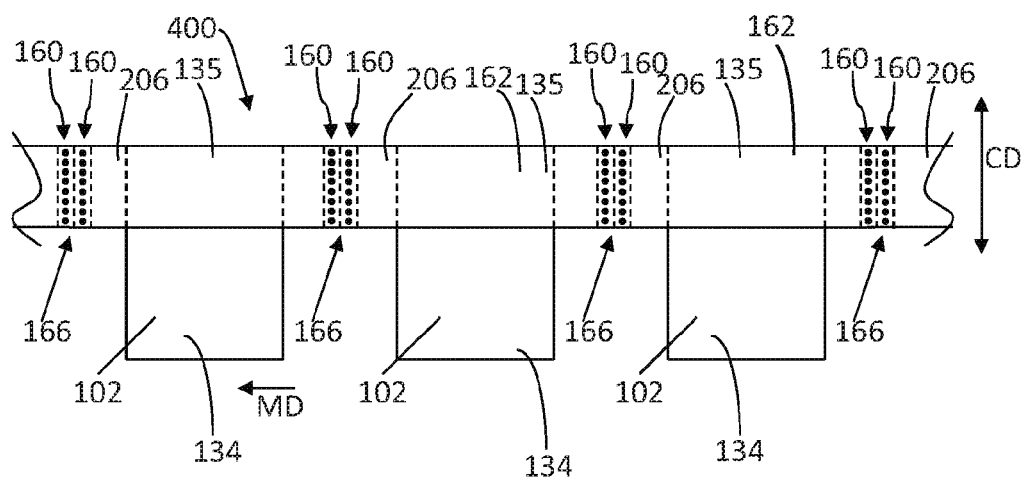
FIG. 4G is a schematic, plan view of a continuous length of folded absorbent articles taken along line 4G-4G in FIG. 4A.

Referring to FIG. 4A, the folded discrete chassis 102 connected with the first and second belt substrates 206, 208 is advanced from the folding apparatus 254 to a bonder apparatus 256. The bonder apparatus 256 operates to bond an overlap area 166 of the first and second belt substrates 206, 208, thus creating discrete bonded regions 160, as shown in FIG. 4G. The overlap area 166 includes a portion of the first belt substrate 206 extending between each chassis 102 and a portion of the second belt substrate 208 extending between each chassis 102.

Figure 4H:
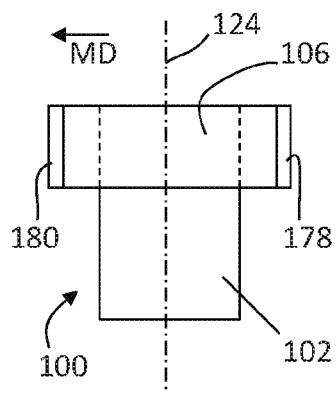
FIG. 4H is a schematic, plan view of a discrete absorbent article in the form of a diaper pant taken along line 4H-4H in FIG. 4A.

As shown in FIG. 4A, the continuous length of absorbent articles 204 are advanced from the bonder apparatus 256 to a cutter 286, shown in the form of a cutting roll for purposes of illustration, where the bonded regions 160 are cut into along the cross direction CD to create a first side seam 178 on a diaper pant 101 and a second side seam 180 on a subsequently advancing diaper pant 101, such as shown in FIG. 4H.

Figure 5:
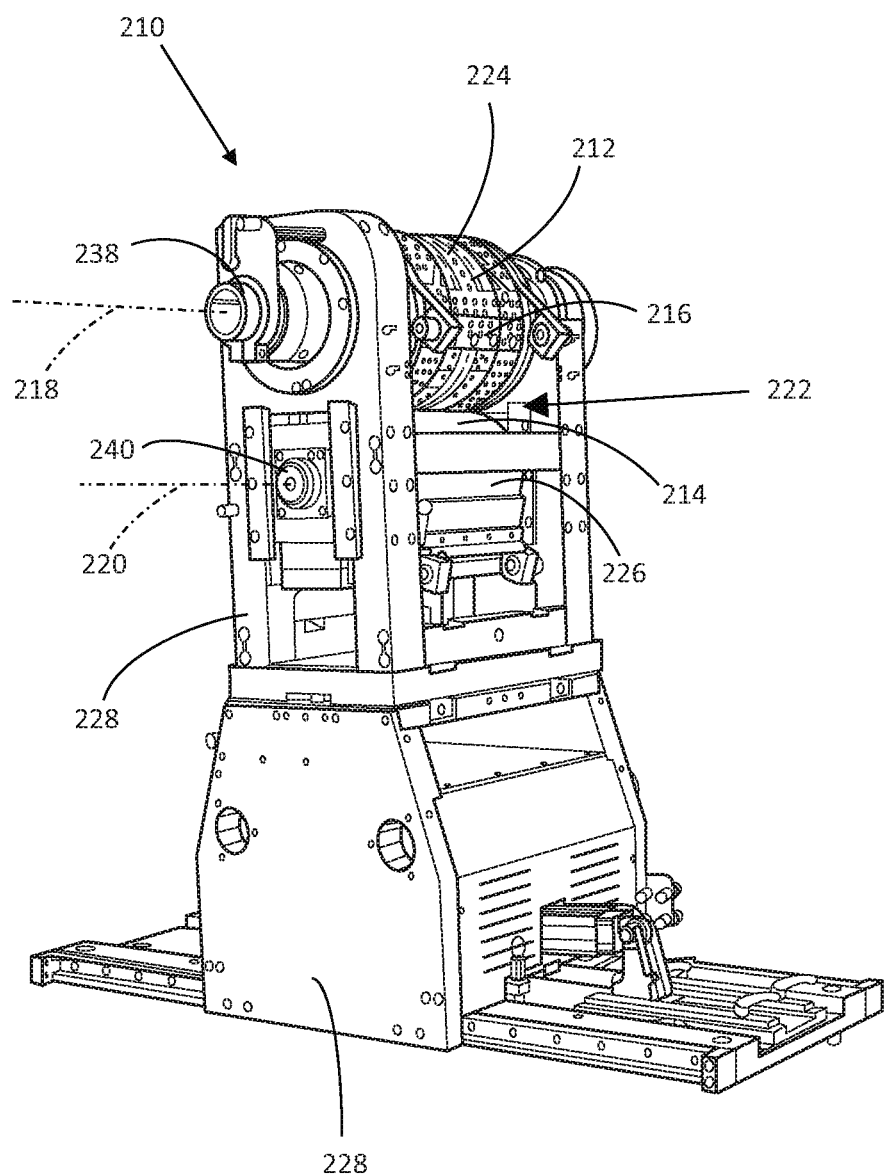
FIG. 5 is a perspective, side view of a rotary cutting apparatus.
Figure 6:
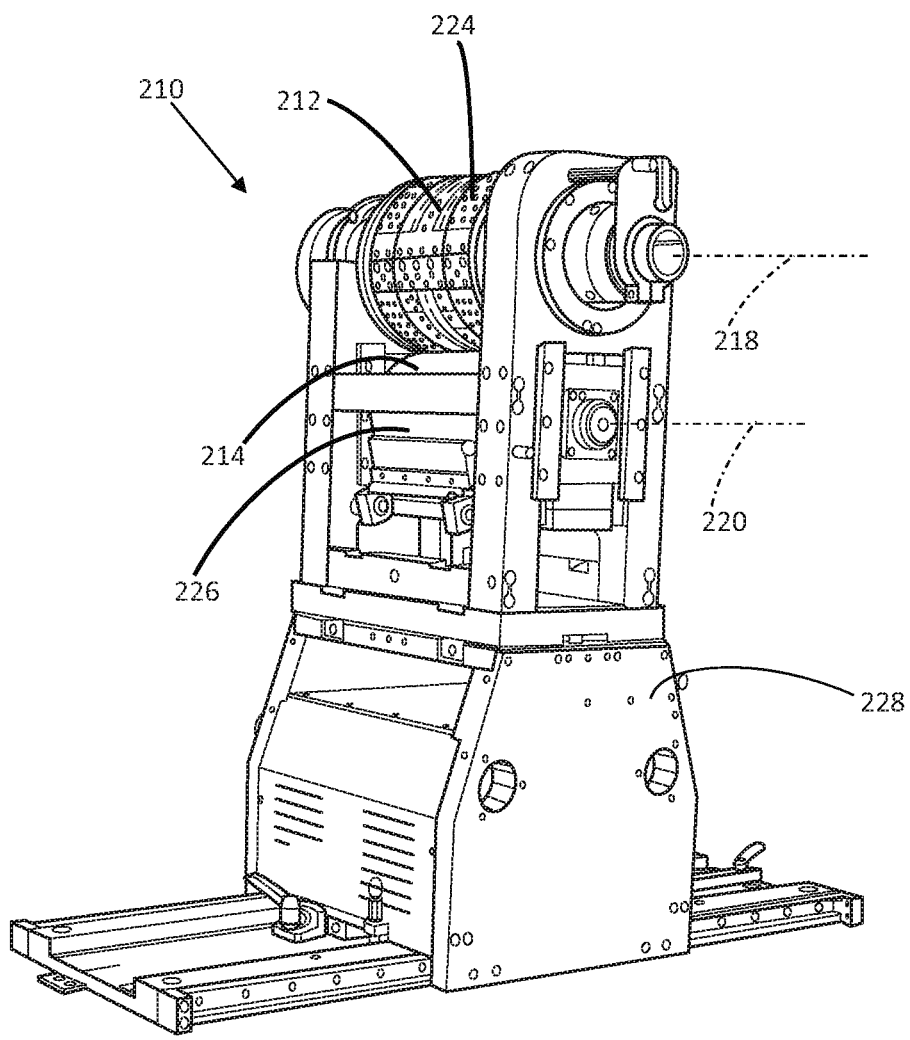
FIG. 6 is a perspective, side view of a rotary cutting apparatus.

As discussed above, the converting apparatus 200 may include a rotary cutting apparatus 210 that may be selectively configurable between a first configuration and a second configuration. For example, FIGS. 5 and 6 show a rotary cutting apparatus having a cutting roll 212 and an anvil roll 214 that are rotatably connected with a frame 228. The cutting roll 212 defines a first longitudinal axis 218 and the anvil roll 214 defines a second longitudinal axis 220. The anvil roll 214 is positioned relative to the cutting roll 212 such that the first longitudinal axis 218 is substantially parallel with the second longitudinal axis 220. The cutting roll 212 and the anvil roll 214 are defined by outer circumferential surfaces 224 and 226, respectively. A cutting member 216 may extend radially outward from the outer circumferential surface 224 of the cutting roll 212.

As shown in FIG. 5, in some exemplary configurations, the cutting roll 212 may be connected with a shaft 238 and the anvil roll 214 may be connected with a shaft 240. The cutting roll 212 and the anvil roll 214 may be connected with the shafts 238, 240 using fixed-floating bearings, for example, that allow for the expansion of components during extended operation. In some exemplary configurations, the anvil roll 214 may rotate independent from the cutting roll 212. For example, the cutting roll 212 and/or the anvil roll 214 may be configured to rotate using gears, belts, or direct couplings. In other exemplary configurations, the anvil roll 214 may be driven by bearer rings on the cutting roll 212. As such, the anvil roll 214 may be a "walking" anvil roll.

Figure 8:
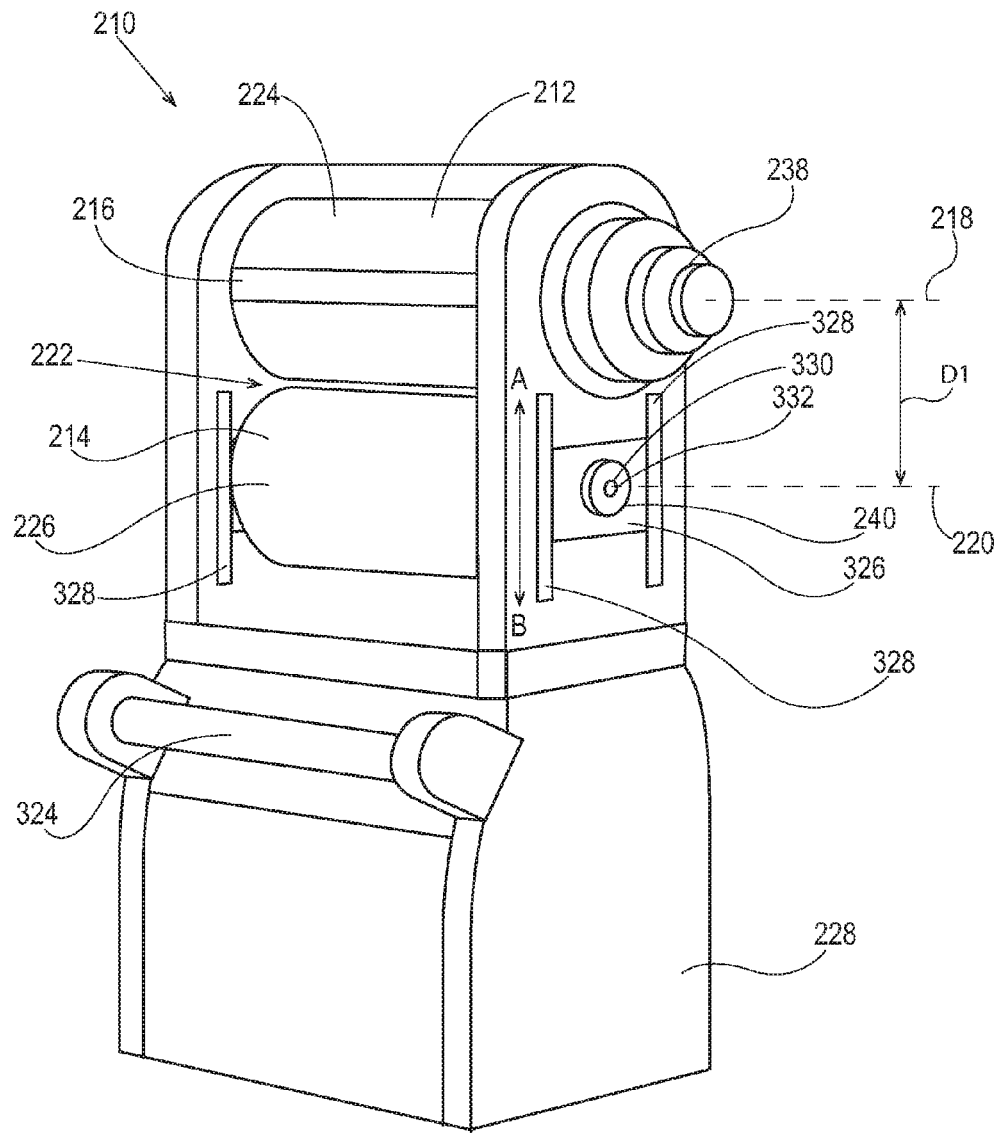
FIG. 8 is a schematic, perspective side view of a rotary cutting apparatus.
Figure 9:
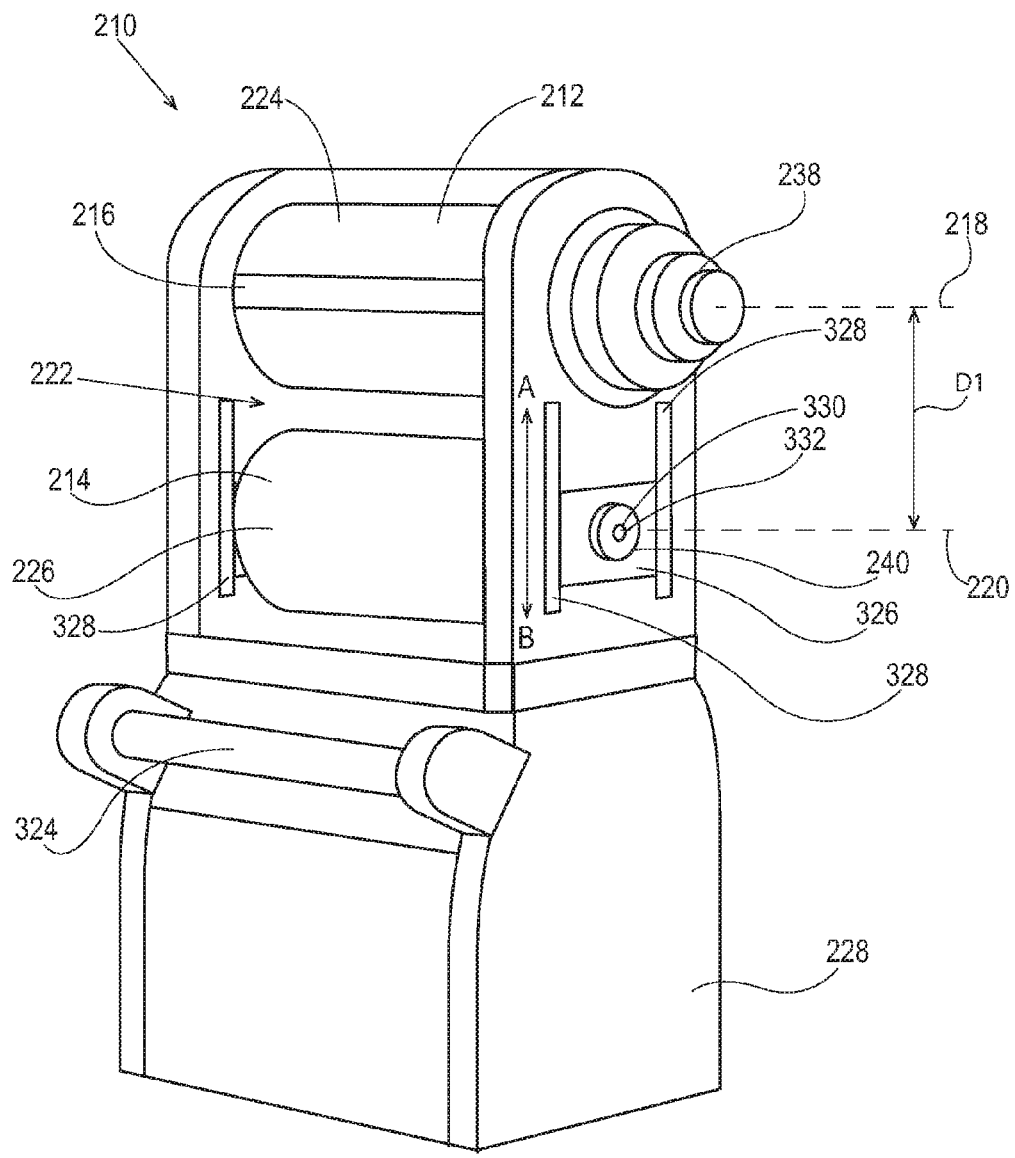
FIG. 9 is a schematic, perspective side view of a rotary cutting apparatus.

The frame 228 may house an anvil bearing block 326 as shown in FIGS. 8 and 9. The anvil bearing block 326 may be coupled with the frame 228. The anvil bearing block 326 may define an opening 332, which may receive bearings 330 for accepting the anvil roll 214. The anvil bearing block 326 may be moveably connected with a guide block 328. The anvil bearing block 326 may selectively move the anvil roll 214 in a first direction A and a second direction B, wherein the first direction A is opposite the second direction B. In some exemplary configurations, the first and second longitudinal axes 218 and 220 are orthogonal to the first and second directions A and B.

The rotary cutting apparatus 210 may be selectively configurable to operate in a substrate cutting configuration and a substrate bypass configuration. Referring to FIGS. 8 and 9, in order to configure the rotary cutting apparatus 210 in the substrate cutting configuration and the substrate bypass configuration, the second longitudinal axis 220 may be selectively movable in the first and second directions A and B between a first position and a second position. As shown in FIG. 8, in the substrate cutting configuration, the second longitudinal axis 220 is located in the first position relative to the first longitudinal axis 218. With the second longitudinal axis 220 in the first position, a first minimum distance $D_1$ is defined between the first longitudinal axis 218 and the second longitudinal axis 220. As shown in FIG. 9, in the substrate bypass configuration, the second longitudinal axis 220 is in the second position relative to the first longitudinal axis 218. With the second longitudinal axis 220 in the second position, a second minimum distance $D_2$ is defined between the first longitudinal axis 218 and the second longitudinal axis 220. The second minimum distance $D_2$ is greater than the first minimum distance $D_1$.

In the substrate cutting configuration, the anvil roll 214 is configured in the first position, such as shown in FIGS. 4A and 8. In operation, the continuous length of chassis assemblies 202 advances onto the outer circumferential surface 224 of the cutting roll 212. Vacuum is applied to the chassis assemblies 202 from the outer circumferential surface 224 of the cutting roll 212. As the continuous length of chassis assemblies 202 advance through the nip 222 between the cutting roll 212 and the anvil roll 214, the cutting member 216 compresses the chassis assemblies 202 against the outer circumferential surface 226 of the anvil roll 214. The force of the cutting member 216 compressing the chassis assemblies 202 toward the anvil roll 214 cuts the continuous length of chassis assemblies 202 into discrete chassis 102. In order for the cutting member 216 to rotate past the anvil roll 214, the cutting member 216 may flex away from the anvil roll 214 as the cutting member 216 compresses the chassis assemblies 202 against the anvil roll 214. As the cutting roll 212 continues to rotate, negative, vacuum pressure may be used to hold the discrete chassis 102 in an extended configuration on the outer circumferential surface 224 of the cutting roll 212. Next, the discrete chassis 102 are transferred to the transfer apparatus 244. Positive air pressure may be applied to the discrete chassis 102 from the outer circumferential surface 224 of the cutting roll to assist in removing of the discrete chassis 102 from the cutting roll 212. In addition, vacuum pressure may be applied to the discrete chassis 102 by the transfer members 248 of the transfer apparatus 244. As a result, the discrete chassis 102 transfers from the cutting roll 212 to the transfer member 248 of the transfer apparatus 244.

Figure 10:
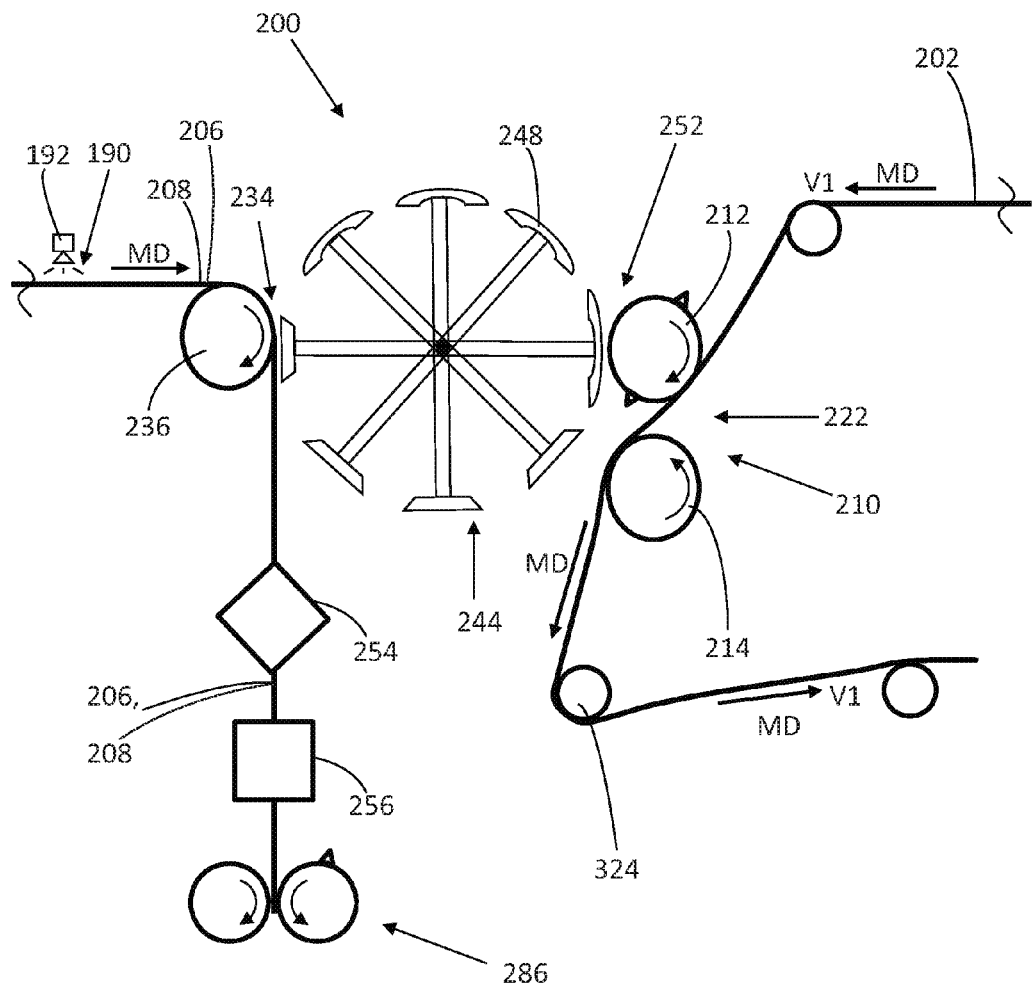
FIG. 10 is a schematic, side elevation view of a converting apparatus.

In the substrate bypass configuration, the anvil roll 214 is configured in the second position, such as shown in FIGS. 9 and 10. A continuous length of chassis assemblies 202 is advanced in a machine direction MD to the outer circumferential surface 224 of the cutting roll 212. In the substrate bypass configuration, the continuous length of chassis assemblies 202 may advance in the machine direction MD at a first speed, V1. The continuous length of chassis assemblies 202 advances through the nip 222 between the cutting roll 212 and the anvil roll 214. The continuous length of chassis 202 advances from the cutting roll 212 to the outer circumferential surface 226 of the anvil roll 214 without the cutting member 216 of the cutting roll 212 cutting the continuous length of chassis assemblies 202. The continuous length of chassis assemblies 202 then advances from the anvil roll 214 to an idler roll 324. From the idler roll 324, the continuous length of chassis assemblies 202 advances away from the flex cutting apparatus 210. It is to be appreciated that the continuous length of chassis assemblies 202 may be collected by an operator at a location away from the rotary cutting apparatus 200.

Once the continuous length of chassis assemblies 202 attains a desired quality, and while the continuous length of chassis assemblies 202 continues to advance on the outer circumferential surface 226 of the anvil roll 214 at the first speed, V1, the rotary cutting apparatus 210 may be placed in the substrate cutting configuration, such as shown in FIGS. 4A and 8. With the second longitudinal axis 220 in the first position, the cutting roll 212 engages the continuous length of chassis assemblies 202. The continuous length of chassis assemblies 202 continue advancing through the nip 222 and the cutting member 216 cuts the continuous length of chassis assemblies 202 into discrete chassis 102. Once the discrete chassis assemblies 102 reach a desired quality with the rotary cutting apparatus 210 in the substrate cutting configuration, the speed of the advancing continuous length of chassis assemblies 202 may be increased to a second speed, V2, that is faster than the first speed, V1, of the continuous length of chassis assemblies 202 advancing in the substrate bypass configuration.

Referring to FIGS. 5 and 6, the cutting member 216 may comprise various materials that are capable of flexing away from the outer circumferential surface 226 of the anvil roll 214. For example, the cutting member 216 may comprise tungsten carbide or tool steel. In other exemplary configurations, the cutting member 216 may comprise a rigid material. In such an exemplary configuration, the cutting roll 212 may be configured with a spring, such as a goose-neck spring, that may be used to flex the cutting member 216 away from the outer circumferential surface of the anvil roll to allow the cutting member 216 to rotate past the anvil roll 214. In some exemplary configurations where the cutting member 216 is a rigid material, the cutting roll 212 may be configured as a rotary die cutter.

The anvil roll 214 may comprise various materials, such as tungsten carbide or tool steel. The outer circumferential surface 226 of the anvil roll 214 may comprise various materials that are integral with, or separate from, the anvil roll 214 material.

As shown in FIGS. 5 and 6, in some exemplary configurations, the cutting roll 212 may be fixed to the frame 228 and the anvil roll 214 may be loaded to the cutting roll 212. In other exemplary configurations, the anvil roll 214 may be fixed to the frame 228 and the cutting roll 212 may be loaded to the anvil roll 214. Various systems may be used to load the anvil roll 214 to the cutting roll 212 or to load the cutting roll 212 to the anvil roll 214. For example, loading systems may include pneumatic cylinders, hydraulic systems, air-over-oil systems, springs, linkages, or actuators. It is to be appreciated that the distance from the axis of rotation 218 of the cutting roll 212 and the axis of rotation 220 of the anvil roll 214 may affect the force applied to the continuous length of chassis assemblies by the cutting member 216.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method comprising the steps of:
advancing a substrate in a machine direction to a rotary cutting apparatus, the rotary cutting apparatus comprising a cutting roll and an anvil roll;
rotating the cutting roll about a first longitudinal axis;
rotating the anvil roll about a second longitudinal axis adjacent to the cutting roll, wherein the anvil roll is positioned relative to the cutting roll such that the first longitudinal axis is substantially parallel with the second longitudinal axis;
placing the rotary cutting apparatus in a first configuration by moving the second longitudinal axis to a first position, wherein the substrate advances to the rotary cutting device in the first configuration at a second speed;
applying vacuum pressure to the substrate such that the substrate is held against an outer circumferential surface of the cutting roll;
cutting the substrate to form discrete components with the rotary cutting apparatus in the first configuration;
holding the discrete components in an extended configuration on the outer circumferential surface of the cutting roll;
placing the rotary cutting apparatus in a second configuration by moving the second longitudinal axis to a second position; and
advancing the substrate at a first speed through the rotary cutting apparatus in the second configuration without cutting the substrate,
wherein the second speed is greater than the first speed.

2. The method of claim 1, wherein when the second longitudinal axis is in the first position, a first minimum distance is defined between the first longitudinal axis and the second longitudinal axis; and
wherein when the second longitudinal axis is in the second position, a second minimum distance is defined between the first longitudinal axis and the second longitudinal axis, and wherein the second minimum distance is greater than the first minimum distance.

3. The method of claim 1, wherein the step of placing the rotary cutting apparatus in the first configuration by moving the second longitudinal axis to the first position further comprises the step of moving the anvil roll in a first direction, wherein the step of placing the rotary cutting apparatus in the second configuration by moving the second longitudinal axis to the second position further comprises the step of moving the anvil roll in a second direction, wherein the first direction is opposite the second direction.

4. The method of claim 3, wherein the first and second longitudinal axes are orthogonal to the first and second directions.

5. The method of claim 3, further comprising a frame, wherein the cutting roll and the anvil roll are rotatably connected with the frame.

6. The method of claim 5, wherein the anvil roll is connected with a bearing, wherein the bearing is rotatably connected with a bearing block, wherein the bearing block is moveably connected with the frame.

7. The method of claim 6, wherein the bearing block is adapted to slide in the first and second directions on the frame.

8. The method of claim 1, wherein the continuous substrate is a continuous length of chassis assemblies.

* * * * *